United States Patent [19]
Pothier et al.

[11] Patent Number: 5,702,463
[45] Date of Patent: Dec. 30, 1997

[54] TIBIAL PROSTHESIS WITH POLYMERIC LINER AND LINER INSERTION/REMOVAL INSTRUMENT

[75] Inventors: Albert Pothier, Memphis; Gregory C. Marik, Germantown; Derrick Givens, Memphis, all of Tenn.

[73] Assignee: Smith & Nephew Inc., Memphis, Tenn.

[21] Appl. No.: 603,445

[22] Filed: Feb. 20, 1996

[51] Int. Cl.⁶ .................. A61F 2/38; A61F 2/30; A61F 2/00
[52] U.S. Cl. .................. 623/20; 623/18; 606/99
[58] Field of Search .................. 623/20, 39, 18; 606/86, 99

[56] References Cited

U.S. PATENT DOCUMENTS

| | | | |
|---|---|---|---|
| 2,789,558 | 4/1957 | Rush | 606/99 |
| 4,364,389 | 12/1982 | Keller | 128/303 R |
| 4,459,985 | 7/1984 | McKay et al. | 128/303 R |
| 4,714,474 | 12/1987 | Brooks, Jr. et al. | 623/20 |
| 5,344,461 | 9/1994 | Phlipot | 623/20 |
| 5,405,396 | 4/1995 | Heldreth et al. | 623/20 |

FOREIGN PATENT DOCUMENTS

| | | | |
|---|---|---|---|
| 634155 | 1/1995 | European Pat. Off. | 623/20 |

Primary Examiner—Michael J. Milano
Assistant Examiner—Tram Anh T. Nguyen
Attorney, Agent, or Firm—Pravel, Hewitt, Kimball & Krieger

[57] ABSTRACT

A tibial prosthesis apparatus and its insertion/removal tool includes a tibial tray that receives a polymeric tray liner with an articulating surface. Dovetail connections are provided for interconnecting the liner and the tibial tray. An instrument is provided that can either insert or remove the liner relative to the tray. The surgeon is provided with cam and hook portions that are at the hooking end of the instrument opposite the lever end. The cam engages the anterior surface of the liner while the hook attaches to the tibial tray and the lever end is rotated to cam the insert into a locked position during insertion. The hook engages the distal side of the liner so that the surgeon can rotate the instrument to disengage or remove the liner from the tray.

12 Claims, 3 Drawing Sheets

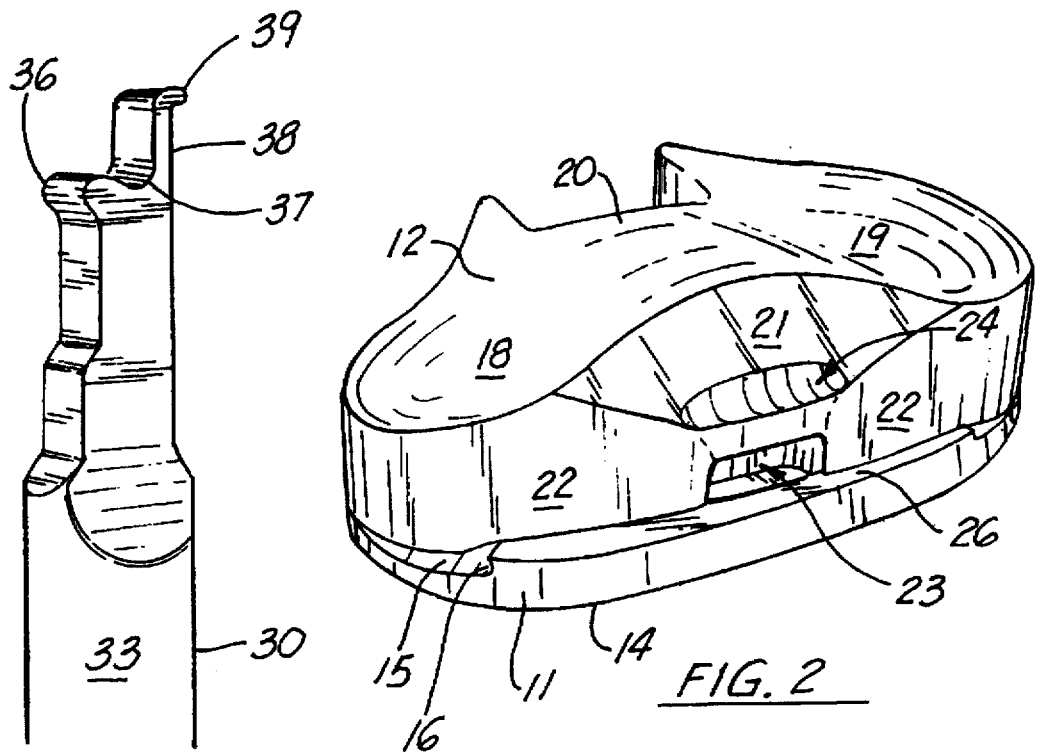
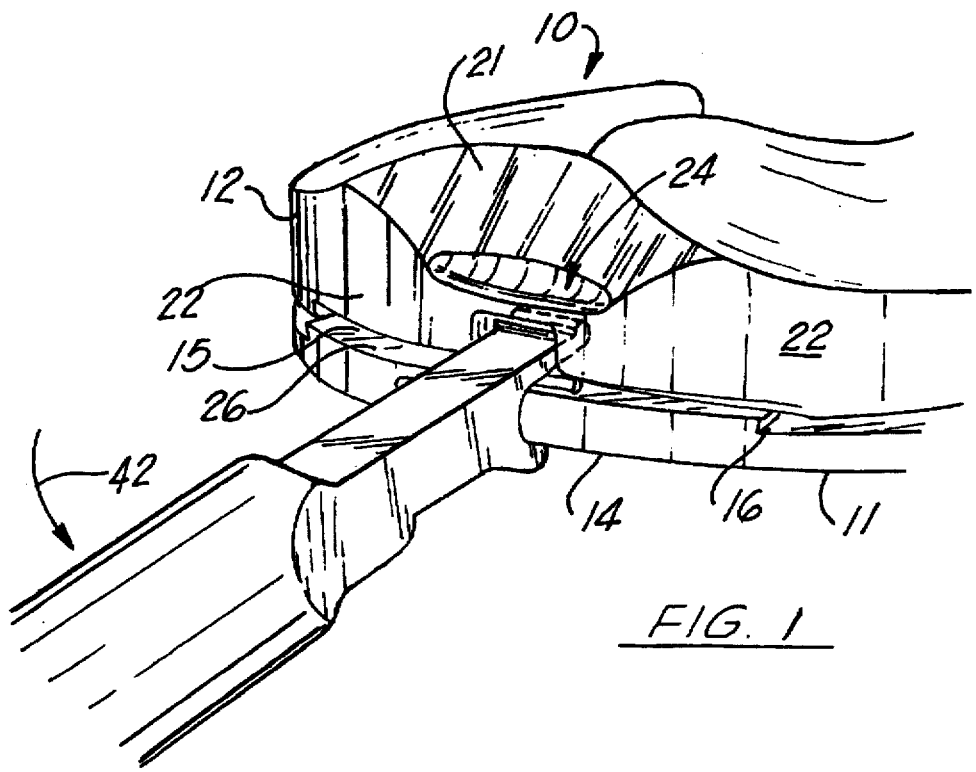

TIBIAL PROSTHESIS WITH POLYMERIC LINER AND LINER INSERTION/REMOVAL INSTRUMENT

BACKGROUND OF THE INVENTION

1. Field of the Invention

The present invention relates to orthopedic surgical prosthetic devices and related instruments and surgical methods. Even more particularly, the present invention relates to an improved tibial prosthesis and instrumentation that both inserts and removes a polymeric liner portion of a prosthesis used in total knee replacement surgery.

2. General Background

Knee joint replacement surgery often requires the surgical implantation of both femoral and tibial components. A surgeon positions the femoral component upon a patient's surgically cut distal femur. A tibial component is surgically implanted on the patient's proximal tibia. It is often desirable to place a number of thicknesses of tibial trial prostheses in sequence on the proximal tibia after a distal femoral component has been positioned. This allows the surgeon to optimize fit. The surgeon tries each of the plurality of different tibial trial prostheses of different articular geometries and thicknesses.

Therefore, there is a need during the surgical procedure to quickly insert and/or remove a number of plastic polymeric liners with respect to the tibial tray that carries them.

Once the tibial base plate is stabilized during a knee operation, a modular trial insert can be used to insure that a thickened cement mantle has not overtightened the joint. This is used with a femoral component. Next, the surgeon takes a polyethylene insert of a chosen thickness and snaps it into place. This tray must be free of all tissue, bone cement, or any other debris to allow for easy insertion. This insert is typically snapped into place by first engaging the heels of the insert posteriorly, pushing all the way into the posterior heel, then snapping the component down anteriorly. The range of motion and ligament stability are checked again.

It is known in the art to push and seat the tibial polyethylene insert into the tibial base using a tibial plastic inserter instrument. This inserter is hammered or tapped distally to lock the tibial insert into position. The surgeon then makes a carefully inspection of the anterior surface of the locking mechanism to insure that the polyethylene insert has fully locked into place in the tibial base.

Instruments that are commercially available for inserting a tibial articular insert into a tibial tray using a gun-type mechanism can be seen in the commercially available Nexgen instrumentation of Zimmer, Inc. This device is in the form of an articular surface inserter that applies both downward and rearward forces to aid in the insertion of the articular surface onto the tibial tray. During use, the surgeon pushes the lever on the inserter fully on either side. The surgeon then places the articular surface onto the implant tray engaging the dove tails. The surgeon steadies the surface of the tray with one hand by applying downward pressure near the posterior cruciate cutout. The surgeon engages the hook on the inserter tool with a mating slot on the front of the plate and closes the lever with the index finger. This is designed to lock the insertion tool to the tray. The surgeon squeezes the handles of the insertion tool to seat the articular surface. Published literature then states that the lever is opened and the insertion tool is removed. Further, it indicates that the surgeon should only insert an articular surface once, never reinserting the same articular surface onto a tibial tray.

Some instruments for removing the tibial implant have been patented. The McKay et al. U.S. Pat. No. 4,459,985 discloses an extractor for dislodging an implanted tibial prosthesis comprising substantially parallel upper and lower members joined by a yoke. The lower member comprises a pair of forked blades to insert under the tibial component and the upper member is adapted to receive a means for applying upward dislodging force. The '985 patent also discusses method used to remove the tibial prosthesis as including the use of an osteotome as a lever by prying under the edge of the tibial tray. This device is for removing the tibial tray and insert for revision surgery, not only the insert.

The Phlipot U.S. Pat. No. 5,344,461 discloses a rotating dovetail attachment mechanism for connecting a modular provisional augmentation block to the distal surface of a provisional tibial tray. The augmentation block has lateral components which contact a vertical surface on a prepare bone. The rotating dovetail attachment mechanism permits the block to be used with a stemmed tibial implant provisional by rotating the lateral components of the augmentation block around the stem during connection of the provisional block to the provisional tibial component.

The Keller U.S. Pat. No. 4,364,389 provides a prosthesis instrument for implanting a pair of separate tibial plates of an endo-knee prosthesis and having a pair of supports with tibia plate locating rods and clamps for rigidly supporting the tibia plates and laterally adjustable for establishing a predetermined implanted relationship thereof.

SUMMARY OF THE INVENTION

The present invention addresses the problem of inserting the tibial insert into the tibial base and/or removing the tibial insert from the tibial base during knee surgery. An object of the present invention is to provide a simple instrument that allows the surgeon to insert or to remove the tibial insert with conjunction of the tibial base locking mechanism.

In the prior art, surgeons have used a range of instruments, including a hammer or a trigger-type gun insertion device in order to solve this problem. However, the present invention provides an advance over these prior art methods and instruments in that a single instrument does both the insertion and removal of the polymeric insert.

The apparatus of the present invention provides a lever type instrument that hooks onto the front of the tibial base and pushes or cams the tibial insert back and down into the dove-tail mechanism provided on the tibial tray or base and with connecting portions on the polymeric insert.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is a partial perspective view of the preferred embodiment of the apparatus of the present invention;

FIG. 2 is a partial perspective view of the preferred embodiment of the apparatus of the present invention;

FIG. 3 is a partial perspective view of the inserter/extractor tool portion of the preferred embodiment of the apparatus of the present invention;

DETAILED DESCRIPTION OF THE PREFERRED EMBODIMENT

Figure 4:
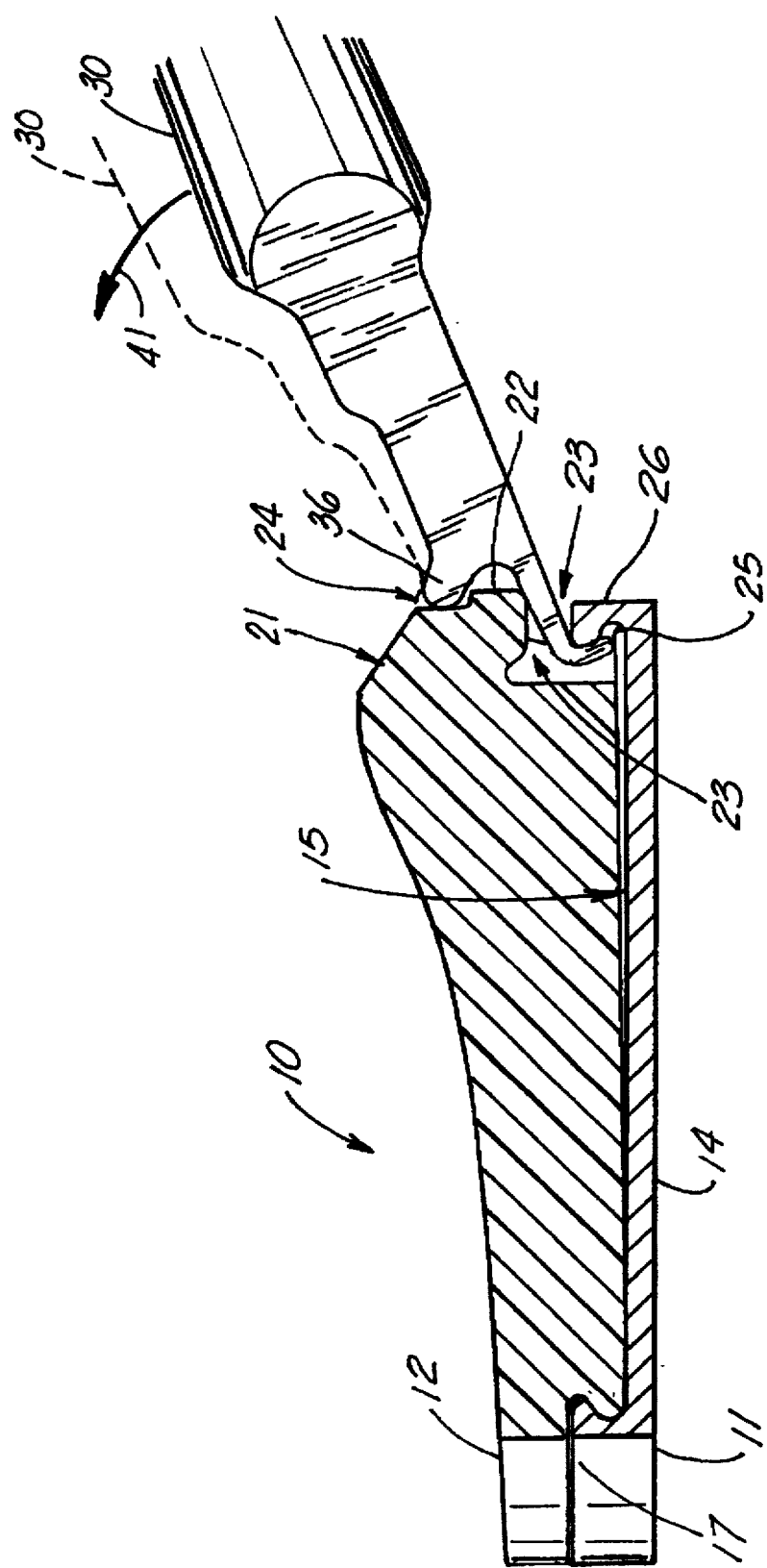
FIG. 4 is a sectional elevational view of the preferred embodiment of the apparatus of the present invention.
Figure 6:
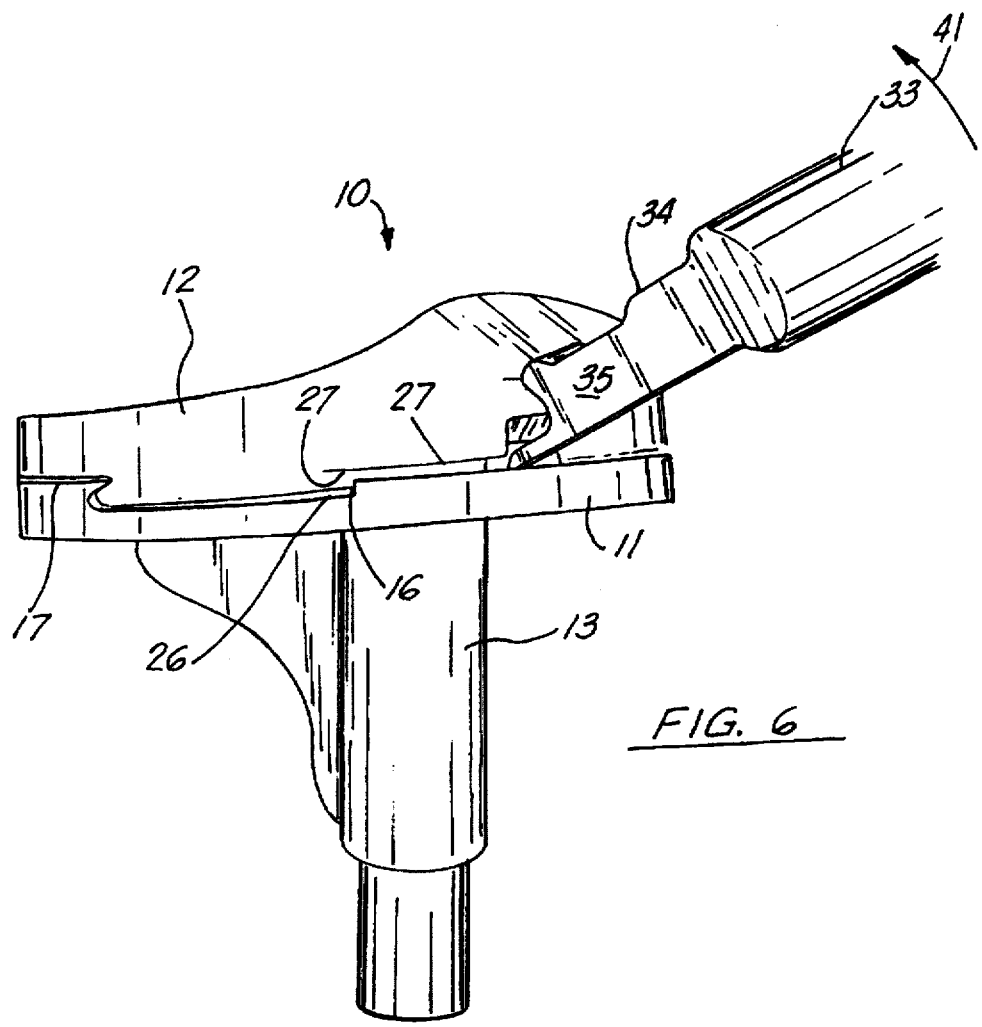
FIG. 6 is a perspective view of the preferred embodiment of the apparatus of the present invention.

FIGS. 1, 4, and 6 show generally the preferred embodiment of the apparatus of the present invention designated generally by the numeral 10. The apparatus 10 of the present invention provides a tibial prosthesis and its insertion/removal tool that can be used during total knee replacement surgery. The apparatus of the present invention includes a tibial tray 11 having a polymeric liner 12. The tray 11 can provide a stem 13 that enters a surgically drilled opening in the patient's proximal tibial generally coincident with the intramedullary canal.

The tibial tray 11 provides a distal surface 14 and a proximal surface 15 that has dovetail connector portions 16, 17. The dovetail connector portions 16, 17 form connections with similar dovetail connecting portions on the polymeric insert 12. These dovetail-type connections per se are known in the art.

The insert or liner 12 has a pair of articulating surface portions 18, 19 separated by a raised portion 20. The anterior surface of the raised portion 20 provides an inclined surface 21 that communicates with anterior surface 22. A socket 23 at the anterior surface 22 receives the inserter instrument 30 as will be described more fully hereinafter during both an insertion and a removal of the liner 12 from the tray 11.

At the intersection between inclined surface 21 and anterior surface 22, a transverse groove 24 is provided. The groove 24 receives a cam portion 36 of inserter tool 30 during an insertion of the liner 12 into the tray 11 as shown in FIGS. 1 and 2.

Another transverse groove 25 is provided between the proximal surface 15 of tray 11 and projecting portion 26. A projecting portion 27 on the insert 12 in FIG. 6 forms the dove-tail connection with dovetail connector portion 16 of projecting portion 26 upon assembly.

Figure 5:
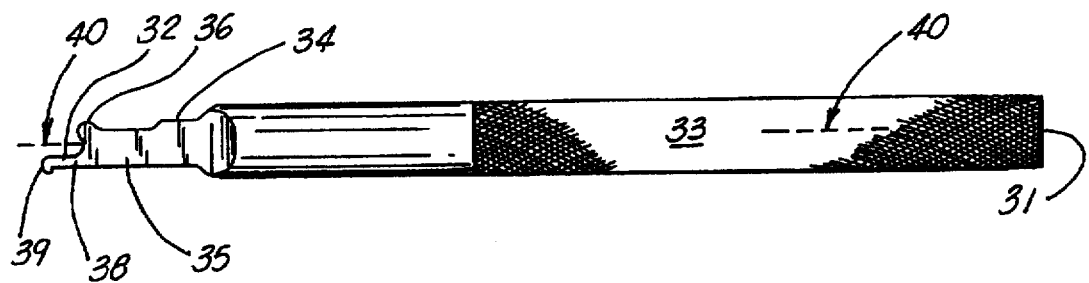
FIG. 5 is a side view of the inserter/extractor tool portion of the preferred embodiment of the apparatus of the present invention.

In FIGS. 3–5, inserter instrument is shown more particularly. The inserter tool instrument 30 has a lever end 31 and a hooking end 32. A handle 33 can be provided so that it can be easily gripped by the surgeon. A shaft portion 34 extends between handle 33 and the hooking 32 end portion of inserter tool 30. Shaft 34 extends from handle 33 and carries a rectangular beam 35 section that is near the hooking end. This rectangular beam section carries a cam 36 and a hook portion 39 with a recess 37 therebetween. The cam portion 36 extends away from the central longitudinal axis 40 of instrument 30 as shown in FIG. 5. The hook portion 39 is mounted upon an extension 38. Hook 39 likewise extends away from axis 40 in a direction that is opposite to the extending direction of cam 36, as shown in FIGS. 5.

In FIGS. 4 and 6, the arrows 41 indicate a rotation of the handle 33 portion of instrument 30 about hook 39 during a camming of insert 12 into its locked position in tray 11. It should be understood that the travel path for insert 12 relative to tray 11 when locking a liner 12 into a tray 11 that has a dovetail locking arrangement is known in the art. The user hooks the posterior edge of the insert 12 into connecting portion 17 of tray 11. The user then pushes the front or anterior surface 22 of the liner to the rear and down. The present invention provides an improved method and instrumentation for accomplishing this interlocking of the liner 12 to the tray 11.

In FIGS. 4 and 6, arrow 41 indicates that the handle 33 is pivoting about hook 39. This places the cam 36 adjacent anterior surface 22 and transverse groove 24. When the surgeon rotates the handle 33 about hook 39, the cam 36 first pushes the insert 12 posteriorly until the rear dovetail locking portion of liner 12 is fully engaged with the connector portion 17 of tray 11. However, continued rotation of the handle 33 about hook 39 registers the cam 36 into groove 24 thus forcing the anterior portion 22 of liner 12 downwardly snapping the projecting portion 27 of insert 12 into the dovetail connector portion 16 of projecting portion 26 of tray 11.

In order to remove the liner 12 from tray 11, the surgeon rotates the instrument 30 one hundred eighty degrees (180°) from the orientation shown in FIGS. 4 and 6. This places the hook portion 39 in an upward direction and the cam 36 in a downward direction as shown in FIG. 1. When the surgeon rotates the handle 33 about hook portion 39, as shown by the arrow 42 in FIG. 1, this lifts the liner 12 anterior portion 22 upwardly and anteriorly thus disengaging the liner 12 from the tray 11.

The following table lists the parts numbers and parts descriptions as used herein and in the drawings attached hereto.

| PARTS LIST | |
|---|---|
| Part Number | Description |
| 10 | tibial prosthesis |
| 11 | tibial tray |
| 12 | polymeric liner |
| 13 | stem |
| 14 | distal surface |
| 15 | proximal surface |
| 16 | dovetail connector |
| 17 | dovetail connector |
| 18 | articulating surface |
| 19 | articulating surface |
| 20 | raised portion |
| 21 | inclined surface |
| 22 | anterior surface |
| 23 | socket |
| 24 | transverse groove |
| 25 | transverse groove |
| 26 | projecting portion |
| 27 | projecting portion |
| 30 | instrument |
| 31 | lever end |
| 32 | hooking end |
| 33 | handle |
| 34 | shaft |
| 35 | rectangular beam section |
| 36 | cam |
| 37 | recess |
| 38 | extension |
| 39 | hook |
| 40 | axis |
| 41 | arrow |
| 42 | arrow |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A tibial knee prosthesis apparatus, comprising:
   a) a tibial tray component having a proximal and a distal surface, said tray being configured to be implanted in a patient's surgically prepared proximal tibia wherein the distal surface fits the tibia along a surface that defines a tibial tray plane;

b) a tibial tray liner insert having a proximal articulating surface for receiving and articulating with a patient's femoral component and an anterior portion with an inclined surface that forms an acute angle with the plane of the tibial tray;

c) a dovetail connection for connecting the liner insert and tibial tray together wherein the liner insert slides along a path during a connecting of the liner and tibial component; and d) an instrument body that enables a user to cam the liner into engagement with the tray, said instrument body having an end portion configured for simultaneously engaging the tray and the liner at the inclined surface while the user moves the liner into engagement with the tray.

2. The tibial prosthesis of claim 1 wherein the instrument enables a user to disengage the insert liner from the tray.

3. The tibial knee prosthesis of claim 1 wherein the tray has a groove at the inclined surface that the instrument attaches to during use.

4. The tibial prosthesis of claim 1 wherein the tray has a slot on its proximal surface that forms a pivot for connecting with the instrument.

5. The tibial prosthesis of claim 1 further comprising a liner with a groove that extends along a medial to lateral direction for receiving the instrument during a separating of the liner from the tray.

6. The tibial prosthesis of claim 1 wherein the tray is metallic and the liner is polymeric.

7. The tibial prosthesis of claim 1 wherein the tray has a peripheral projecting portion and the liner has a peripheral recess that forms a connection with the peripheral projecting portion of the tray.

8. A tibial knee prosthesis apparatus, comprising:

a) a tibial tray component having a proximal and a distal surface, said tray being configured to be implanted in a patient's proximal tibia;

b) a tibial tray liner insert having a proximal articulating surface for receiving and articulating with a patient's femoral component;

c) a dovetail connection for connecting the liner insert and tibial tray together wherein the liner insert slides along a path during a connecting together of the liner and the tibial component;

d) an instrument body that enables a user to cam the liner into engagement with the tray, said instrument body having an end portion configured for engaging both the tray and the liner while the user moves the liner into engagement with the tray; and e) wherein the liner has a groove that forms a connection with the instrument body when the user engages the liner with the instrument body.

9. A tibial knee prosthesis apparatus, comprising;

a) a tibial tray component having a proximal and a distal surface, said tray being configured to be implanted in a patient's proximal tibia;

b) a tibial tray liner insert having a proximal articulating surface for receiving and articulating with a patient's femoral component;

c) a dovetail connection for connecting the liner insert and tibial tray together wherein the liner insert slides along a path during a connecting together of the liner and the tibial component;

d) an instrument body that enables a user to cam the liner into engagement with the tray, said instrument having an end portion configured for engaging both the tray and the liner while the user moves the liner into engagement with the tray; and e) wherein the instrument body has central longitudinal axis, a lever end portion, and a hooking end portion, the hooking end portion comprising a pair of spaced apart projections extending away from said axis.

10. A tibial knee prosthesis apparatus, comprising:

a) a tibial tray component having a proximal and a distal surface, said tray being configured to be implanted in a patient's proximal tibia;

b) a tibial tray liner insert having a proximal articulating surface for receiving and articulating with a patient's femoral component;

c) a dovetail connection for connecting the liner insert and tibial tray together wherein the liner insert slides along a path during a connecting together of the liner and the tibial component;

d) an instrument body that enables a user to cam the liner into engagement with the tray, said instrument body having an end portion configured for engaging both the tray and the liner while the user moves the liner into engagement with the tray.

e) the instrument body has central longitudinal axis, a lever end portion and a hooking end portion, the hooking end portion comprising a pair of spaced apart projections extending away from said axis; and f) wherein the instrument body includes a handle at the lever end portion and the projections are spaced longitudinally apart at differing distances from the handle.

11. A tibial knee prosthesis apparatus, comprising:

a) a tibial tray component having a proximal and a distal surfaces and a peripheral projecting portion that extends a partial distance about the periphery of the tray, said tray being configured to be implanted in a patient's proximal tibia;

b) a tibia tray liner having an anterior portion that has a socket that communicates with the tray, an inclined surface, and a proximal articulating surface for receiving and articulating with a patient's femoral component and a peripheral recess portion;

c) the peripheral projecting portion of the tray and the peripheral recessed portion of the liner defining a connection for connecting the liner and tibial tray together wherein the liner slides along path during a connecting of the liner and tibial component;

d) an instrument that enables a user to cam the liner into engagement with the tray, said instrument having a lower end portion configured for simultaneously engaging the tray and the liner at the inclined surface while the user moves the liner into engagement with the tray; and e) wherein the instrument enables a user to disengage the liner from the tray while the lower end portion of the instrument occupies the socket during disengagement, and wherein rotation of the instrument handle about the end portion enables such disengagement.

12. The tibial prosthesis of claim 11 wherein the instrument enables a user to disengage the insert liner from the tray.

* * * * *